(12) United States Patent
Flannery et al.

(10) Patent No.: US 7,892,485 B1
(45) Date of Patent: Feb. 22, 2011

(54) CLEANING OF SPONGES

(75) Inventors: Matthew Flannery, Astoria, NY (US);
Tod Maitland, New York, NY (US);
Peter Schon, New York, NY (US)

(73) Assignee: T&M Innovations Inc., Astoria, NY (US)

( * ) Notice: Subject to any disclaimer, the term of this patent is extended or adjusted under 35 U.S.C. 154(b) by 528 days.

(21) Appl. No.: 11/873,687

(22) Filed: Oct. 17, 2007

Related U.S. Application Data (60) Provisional application No. 60/829,845, filed on Oct. 17, 2006.

(51) Int. Cl.
*A61L 2/18* (2006.01)
*A47L 13/14* (2006.01)

(52) U.S. Cl. .......................................... 422/28; 15/261

(58) Field of Classification Search .................. 422/28, 422/292, 294, 297, 300, 301; 206/207; 15/261
See application file for complete search history.

(56) References Cited

U.S. PATENT DOCUMENTS

| 3,276,064 A | * | 10/1966 | Moore .......................... 15/261 |
| 6,270,275 B1 | | 8/2001 | Martz |
| 7,041,261 B2 | | 5/2006 | Margolis |

* cited by examiner

*Primary Examiner*—Walter D Griffin
*Assistant Examiner*—Timothy Cleveland
(74) *Attorney, Agent, or Firm*—Gerry J. Elman; Elman Technology Law, P.C.

(57) ABSTRACT

A device for cleaning and deodorizing a sponge and a method of using the device. The device includes a carrier assembly that travels along a guide-track system and is lowered into a base unit large enough to hold a bath of cleaning solution that would engulf the sponge. The carrier assembly is used to compress, decompress, and recompress the sponge, which in turn absorbs a cleaning solution and expels the cleaning solution along with foreign matter.

2 Claims, 9 Drawing Sheets

CLEANING OF SPONGES

CROSS REFERENCE TO RELATED APPLICATIONS

This application claims the benefit under 35 U.S.C. §119(e) from U.S. Provisional Patent Application 60/829,845 filed Oct. 17, 2006, the entire contents of which are incorporated herein by reference.

BACKGROUND OF THE INVENTION

This invention concerns a device for cleaning and deodorizing sponges and a method of preventing or greatly reducing microbial contamination of household or commercial sponges.

Sponges are commonly used for cleaning surfaces or wiping liquids. Both natural and synthetic (e.g. cellulose) sponges assist with household and commercial cleaning in various areas, especially where food is being prepared. Because sponges are used to retain liquids and clean surfaces that may be infected, a wet or damp sponge used repeatedly provides a significant opportunity for the proliferation of bacteria or other harmful microbes. Sponges frequently become carriers of bacteria such as pseudomonas, *staphylococcus, salmonella, E. coli,* and *listeria.* An unclean sponge can spread infection rather than prevent infection by introducing bacteria to every surface it contacts during use.

Currently, the Environmental Protection Agency regulates the efficacy of disinfecting agents and devices for hard, flat, non-porous surfaces, but not for soft, porous materials such as sponges. As explained above, sponges, because of their porous and absorptive nature, are more prone to harbor and spread harmful microbes than hard surfaces. In spite of this and perhaps because of the lack of regulation by the Environment Protection Agency, current methods for disinfecting sponges are ineffective and in some cases pose health risks independent of the microbes they are designed to eliminate.

Examples of methods currently used to prevent the spread of infection by unclean sponges include soaking a sponge in a mix of bleach and water, exposing the sponge to microwaves, spraying antibacterial aerosol products on the sponge, or disposing of the sponge. The use of bleach mixtures with cleaning agents or aerosols creates a risk of exposure to hazardous fumes. Using microwaves can cause toxic fumes and disposable sponges can be costly and create waste. Sponges pre-infused with disinfectant can be dangerous because of the toxicity of the chemicals used. Thus, there is a need for a simple, inexpensive, safe, and effective system for preventing or greatly reducing microbial contamination of sponges.

SUMMARY OF THE INVENTION

The invention involves a sponge-cleaning device and method wherein a sponge is placed in a vertically-oriented carrier assembly, compressed between a pair of perforated carrier elements and immersed in a cleaning solution. Compression is then released, whereupon the sponge expands and imbibes the solution. Compression force is then re-imposed on the sponge, squeezing out much of the imbibed solution and leftover particles, such as pieces of food, from the sponge. The carrier assembly is then withdrawn from the device, releasing the cleaned sponge for use.

A preferred device of the present invention comprises a base unit having a bath for containing liquid, having a generally rectangular interior floor, an opening at the top, and walls of sufficient height that when a carrier assembly for a kitchen sponge is vertically inserted into the top of the base unit, the sponge is submerged in the liquid therein.

The carrier assembly comprises a pair of generally planar carrier elements that support a household sponge in vertical orientation for insertion and removal from the housing. The carrier elements may be hinged together along their respective bottom edges, so that they open and close like a jaw, and desirably they have handles formed along the respective top edges of the carrier elements. To facilitate movement of liquid into and out of the sponge being cleaned, the surface of the carrier elements in contact with the sponge have a multiplicity of openings. Desirably each carrier element may have a paddle-like generally rectangular plastic body with perforations formed or drilled therethrough.

The carrier assembly is desirably configured to be inserted and withdrawn from the bath in the base unit with its path being stabilized via a guide-track system. Desirably the guide-track system is formed into the top opening of the base unit.

The base unit contains a solution for cleaning sponges. The carrier assembly and guide-track system may be configured such that the carrier assembly is pulled up along the track and holds its position at a point in its vertical path, so that the user may release his grip on the carrier assembly and the carrier elements open from the force of gravity. A sponge may be disposed in the carrier assembly and aligned generally vertically much like a slice of bread in a pop-up toaster. The configuration may also enable the carrier elements to open when the carrier assembly is immersed in the solution. Desirably, the device incorporates at least one detent to keep the carrier assembly fixed at a point along its vertical path. Preferably the point is near the apex of the carrier assembly's path, so that the carrier assembly or sponge is not in contact with the solution and is allowed to dry.

To operate the device, a sponge is placed in the carrier assembly and squeezed, causing the paddle-like interior surfaces of the carrier elements to move closer together as it is lowered into the base unit and immersed within the solution. At the bottom of the carrier assembly's path, the compression exerted on the carrier elements is relieved allowing the sponge to decompress and thereby absorb the solution surrounding it. The sponge may remain in the liquid for whatever duration is deemed to provide optimal decontamination. The period for soaking the sponge in the cleaning solution depends on the extent of contamination of the sponge and the type of solution in the bath, such as a sanitizer or disinfectant. Prior to lifting the carrier assembly vertically out of the cleaning solution, the compression is reapplied and maintained to force out solid debris and solution absorbed by the sponge. In many uses, the sponge can be removed almost immediately after the aforementioned step.

In one aspect, the present invention provides a device for decontaminating a sponge. This device comprises a carrier assembly for compressing a sponge and immersing it in cleaning solution and a base unit comprising a bath for containing cleaning solution, having a generally rectangular interior floor, an opening at the top and walls of sufficient height that when a kitchen sponge is vertically inserted via the carrier assembly into the base unit, the sponge is immersed in the cleaning solution therein.

In another aspect, the present invention provides a method of cleaning a sponge comprising the steps of compressing a sponge to be cleaned in a carrier assembly, lowering the compressed carrier assembly to immerse the sponge in a cleaning solution, releasing compression to allow the sponge to absorb the solution, compressing again to expel absorbed liquid along with foreign matter, raising the compressed carrier assembly from the solution, and removing the sponge for use.

In preferred embodiments of the present invention, the carrier assembly comprises a pair of paddle-like carrier elements hingedly attached along their bottom edges. The carrier elements have channels for cleaning solution to enter and exit a sponge during operation of the device. Such channels may be provided by a multiplicity of perforations through the carrier elements, or other means for providing a pathway for the cleaning solution.

In another aspect, the present invention further comprises a guide-track system to guide the carrier assembly along a vertical path and at least one detent to hold the carrier assembly at a point along its vertical path within the guide-track system. It is an advantage of the invention that providing at least one detent to maintain the carrier elements at a point near the apex of its vertical path above the surface of the cleaning solution in the base unit will allow the sponge to dry. It is yet another advantage of the invention that maintaining the carrier elements at point near the apex of its vertical path will keep the carrier elements open and in a position to readily receive a sponge, thus eliminating the need to lift or hold the carrier elements above the solution to insert a sponge.

It is an advantage of the invention that compressing the sponge prior to immersion into the cleaning solution in the base unit and then allowing the sponge to decompress while immersed within the base unit allows the sponge to more effectively absorb the solution.

It is another advantage of the invention that the cleaning device provides two modes of decontaminating a sponge. The first mode is achieved by destroying as many microorganisms as possible present in the sponge by immersing the sponge in a disinfectant or sanitizer. The second mode is achieved by compressing the sponge prior to insertion, decompressing the carrier assembly allowing the sponge to absorb the cleaning solution, and again compressing the carrier assembly to expel cleaning solution, as well as foreign particles and microbes entrained in the sponge prior to lifting the carrier assembly out of the solution.

It is another aspect of the invention that the device further comprises a spring in the base unit to assist in lifting the carrier assembly out of the solution and a detent to lock the carrier assembly at a point at the bottom of its vertical path against the spring.

It is an advantage of the invention that the sponge cleaning device is of simple construction and economical to manufacture. It is an advantage of the invention that the device could be made of plastic which can be easily molded and light weight. Other materials such as stainless steel and ceramic could also be used for a more high-end market.

It is another advantage of the invention that the sponge cleaning device itself can be easily disassembled to clean by either hand washing or machine washing.

It is yet another aspect of the invention that the base unit is filled with an effective and affordable solution that is not a skin irritant or caustic and could be of an environmentally friendly nature.

It is another aspect of the invention that certain embodiments of the invention are capable of being used standing on a horizontal surface or mounted to a vertical surface.

It is another aspect of the invention that the base unit is weighted in order to counter the upward forces applied by a user when lifting the carrier elements out of the solution. It is another aspect of the invention that the detachable base has a non-slip bottom surface to prevent the device from sliding during use. It is another aspect of the invention that the unit has a mounting bracket for suction cups to allow it to stick to the side of a sink or can be mounted with screws inside a cabinet.

In preferred embodiments of the invention, the device has dimensions appropriate to accept a household sponge and to be stored conveniently on a counter-top. For example, a small cellulose household sponge would typically have dimensions of 4.5 inch×3 inch×0.5 inch, whereas a large household sponge would typically be 8 inch×4.5 inch×1.5 inch. An advantage of the invention is that the device can alternatively be manufactured with increased or decreased size so that such an embodiment would accommodate a sponge having a size outside this range.

These and other aspects and advantages of the present invention will become readily apparent from the following detailed description taken in conjunction with the accompanying drawings.

DETAILED DESCRIPTION

Figure 1:
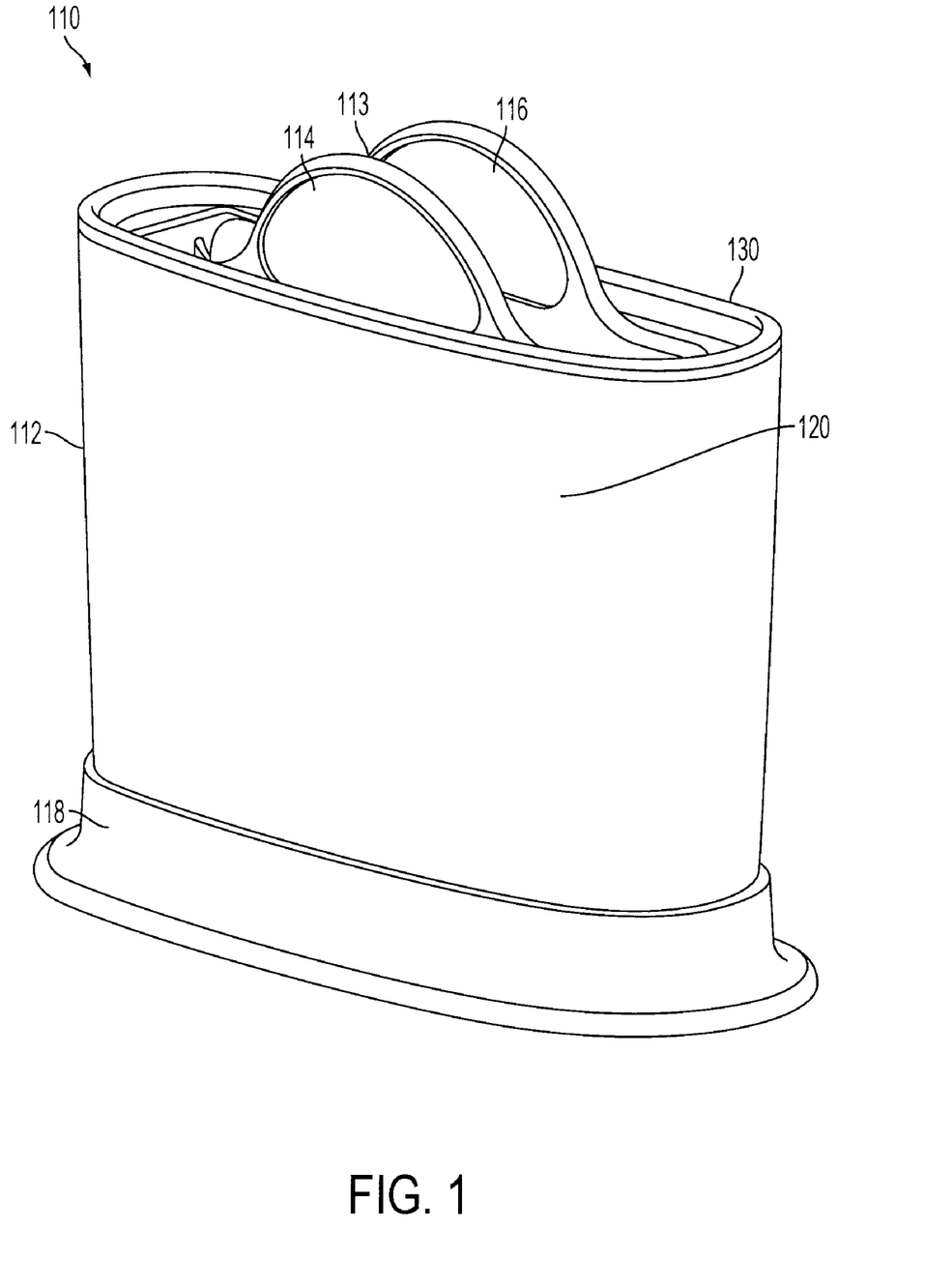
FIG. 1 is a front perspective view of a first embodiment of a sponge cleaning device of the present invention in its closed, immersed state.

FIG. 1 shows a first embodiment of the sponge cleaning device 110 comprising a base unit 112 and a carrier assembly 113 formed of a hinged pair of perforated carrier elements 114 and 116 that are inserted from the top, passing through an integrally connected cap 130, and down into the base unit 112. Device 110 cleans sponges in accordance with the method of the present invention. The user places a sponge between the perforated carrier elements 114 and 116 and while compressing carrier elements 114 and 116, pushes downwardly on the carrier assembly, causing the carrier elements and sponge to travel downwardly into the base unit 112.

The base unit 112 comprises a bath 120 and a detachable base 118 which enables cleaning device 110 to stand on a horizontal surface such as a counter-top. Desirably, the base unit 112 is weighted to counter the forces applied to perforated carrier elements 114 and 116 during use. It is also desirable that detachable base 118 has a non-slip bottom surface for stability. Bath 120 is filled with a cleaning solution. The depth of base unit 112 and the opening in the top of base unit 112 through which paddle-like carrier elements 114 and 116 are inserted should be sufficiently deep and wide, respectively, so that a sponge can be easily and completely immersed in the cleaning solution.

Figure 2:
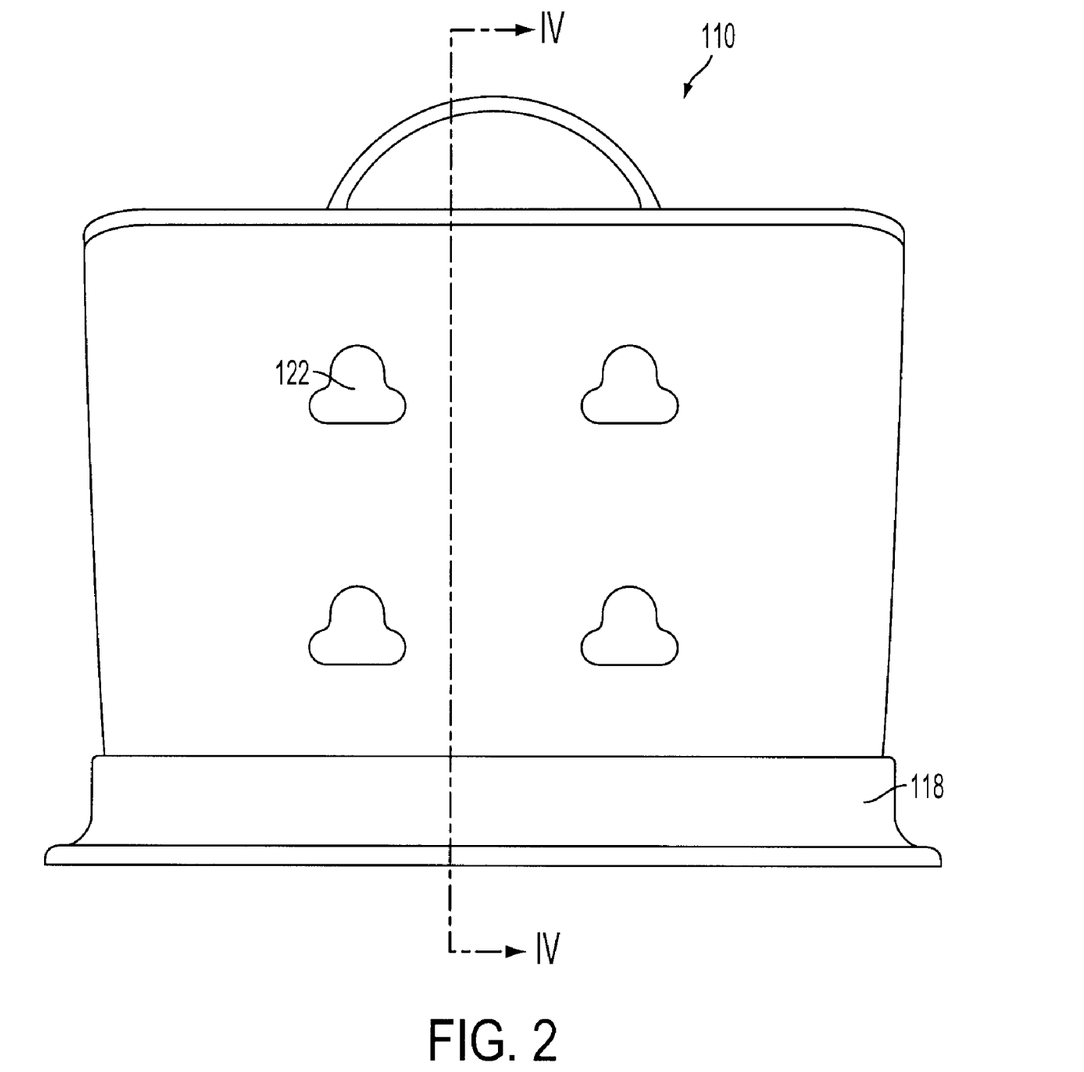
FIG. 2 is a rear perspective view of the sponge cleaning device of FIG. 1.

Referring now to FIG. 2 which is a rear view of the first embodiment of the cleaning device 110, the device 110 is capable of being mounted on a vertical surface, such as a sink, wall or cabinet door above a sink, by having a plurality of indents 122 shaped to receive the head of a nail, screw, or suction cup. Vertical storage is further facilitated by removing detachable base 118. The ability to mount the sponge cleaning device on a vertical surface provides added convenience and access to the cleaning device in areas where sponges are commonly used. Alternative means of mounting the device 110 onto a wall, sink, or cabinet include, but are not limited to, suction cups, adhesives, hooks, or hook-and-loop tape such as Velcro® (Velcro Industries B.V.). The option to mount the device on a vertical surface is also advantageous in areas where space on a horizontal surface is limited or it is desired to keep the device out of the reach of young children.

Figure 3:
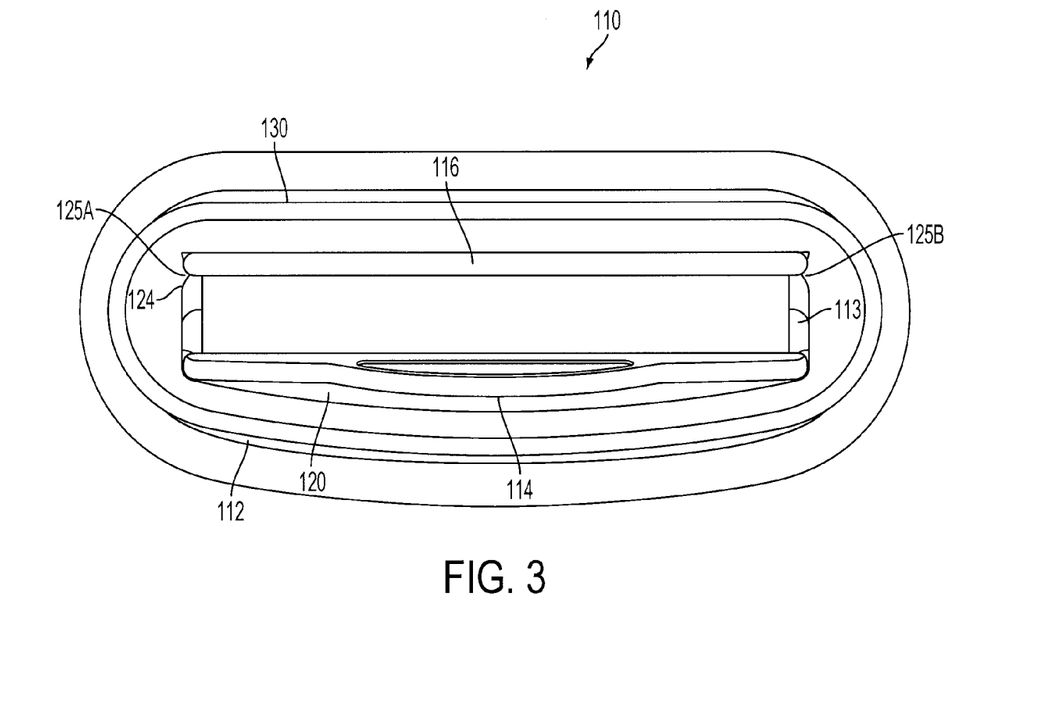
FIG. 3 is a plan view of the sponge cleaning device of FIG. 1.

FIG. 3 is a plan view of the first embodiment of the cleaning device 110. Paddle-like carrier elements 114 and 116 are hingedly attached along their respective bottom edges. The carrier elements 114 and 116 are vertically inserted into the top of the base unit 112, hinge first. While carrier element 116 is inserted, it slides through a guide-track system 124 comprising guide-tracks 125A and 125B that keep the carrier element 116 aligned in a vertical position. The distance between the guide-track 125A and 125B is greater than the length of the hinge connecting carrier elements 114 and 116, thus allowing the carrier assembly 113 to be removed from base unit 112 for hand or machine washing. The guide-track system 124 is integrally connected to a cap 130, which has an opening through which carrier elements 114 and 116 and a sponge can pass and is affixed to the top of base unit 112.

Figure 4:
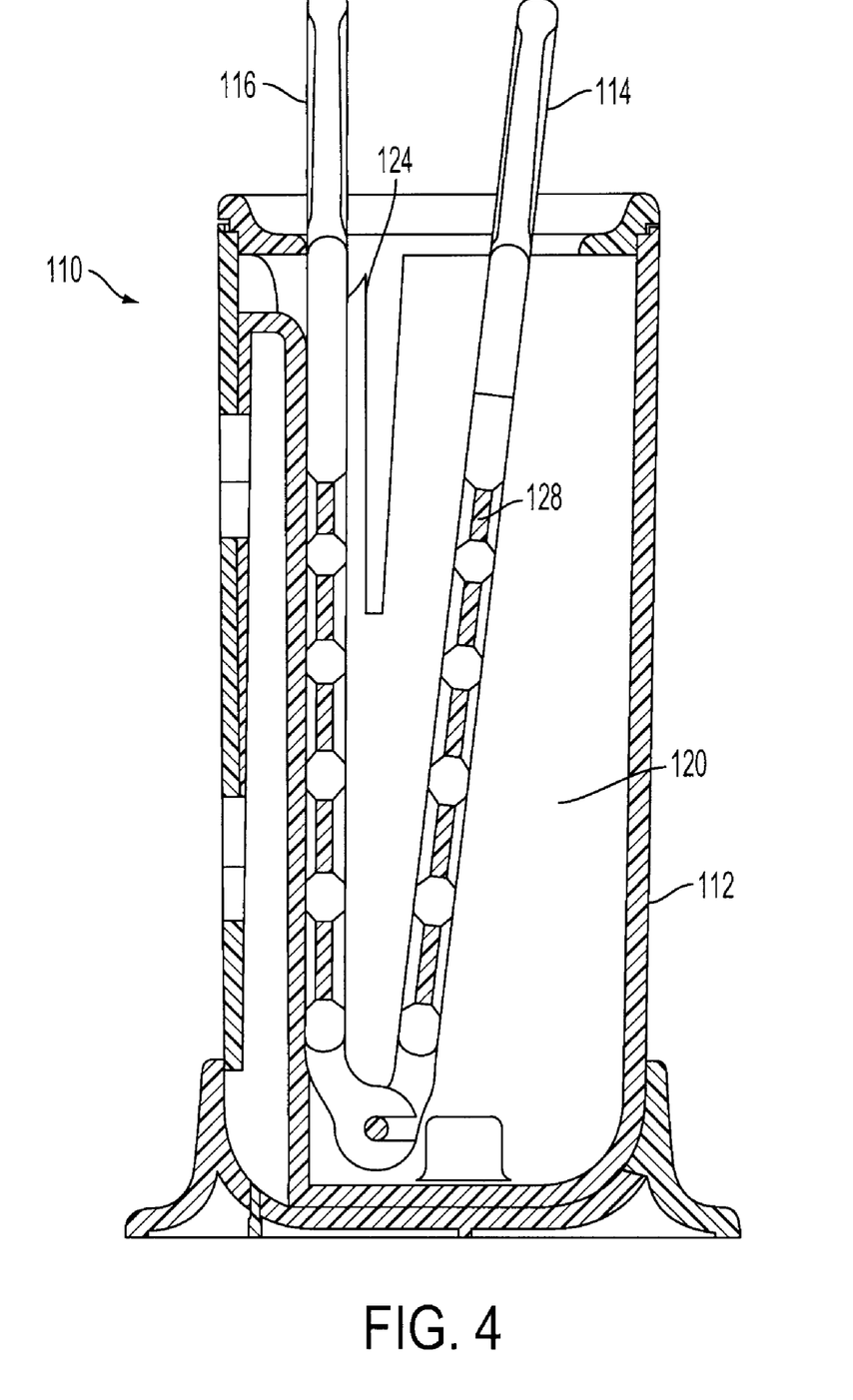
FIG. 4 is a cross-sectional view of the sponge cleaning device of FIG. 2, taken along line IV-IV, showing both carrier elements inserted in the base unit.

FIG. 4 is a cross-sectional view of the first embodiment of the cleaning device 110, taken along line IV-IV of FIG. 2. FIG. 4 shows a side wall of base unit 112 removed to reveal carrier elements 114 and 116 inserted into bath 120. Each of the carrier elements 114 and 116 has openings such as the multiplicity of perforations 128 through which the cleaning liquid may be absorbed and expelled with foreign matter. In order to clean a sponge, the sponge is inserted into the carrier assembly between carrier element 114 and carrier element 116, which are then compressed and lowered vertically into bath 120 so that carrier element 116 slides through guide-track system 124. Bath 120 contains a cleaning solution which is drawn into the sponge through perforations 128. When the sponge is fully immersed, carrier elements 114 and 116 are decompressed, like a partially opening jaw, allowing the sponge to expand. Before the user lifts the carrier assembly out of bath 120, paddle-like carrier elements 114 and 116 are again squeezed together, compressing the sponge to expel from the sponge cleaning liquid and infectious or solid waste that had been entrained within the sponge.

Figure 5:
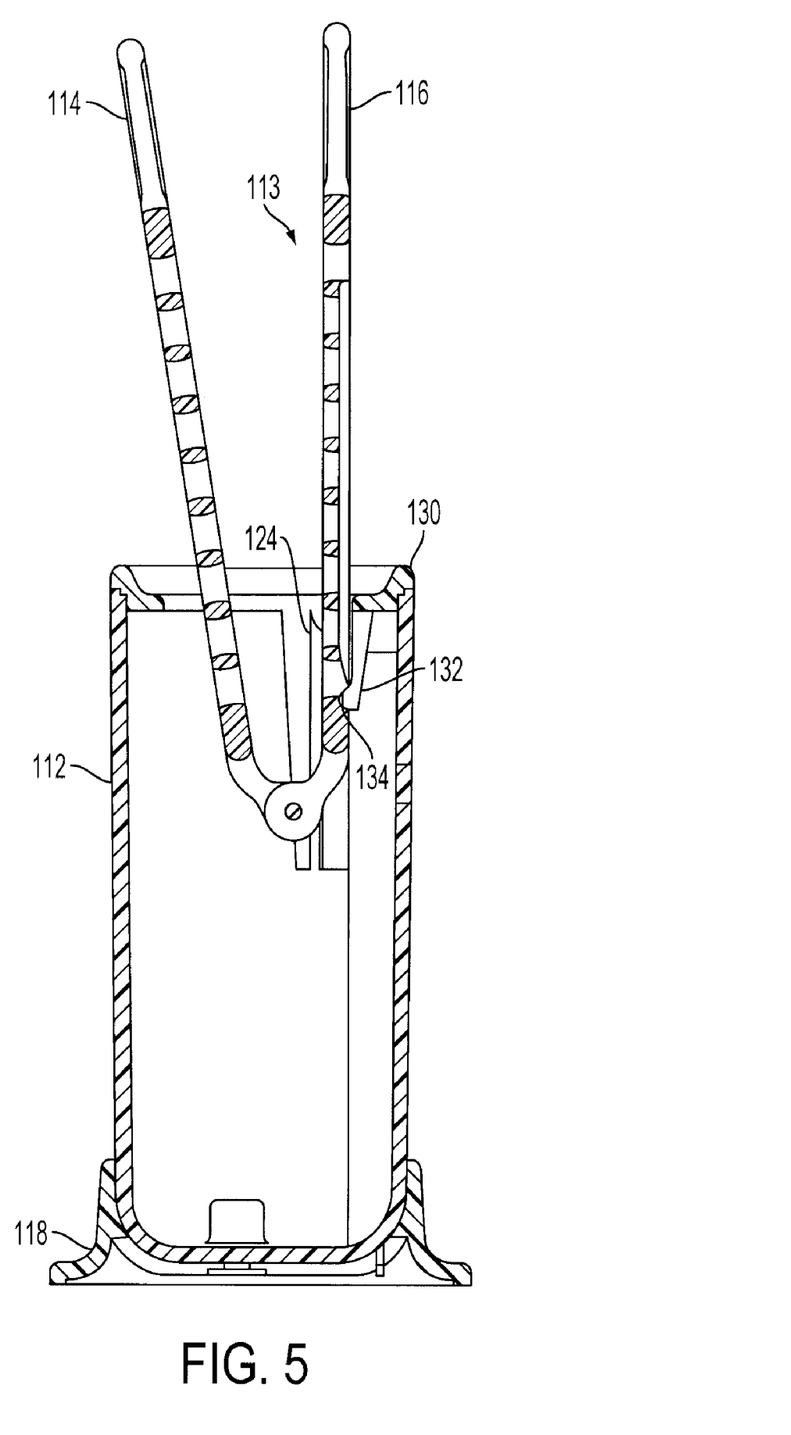
FIG. 5 is a cross-sectional view the sponge cleaning device of FIG. 6, taken along line V-V, showing the carrier assembly locked in a position near the apex of its vertical path by a detent. The sponge has been removed for clarity.
Figure 6:
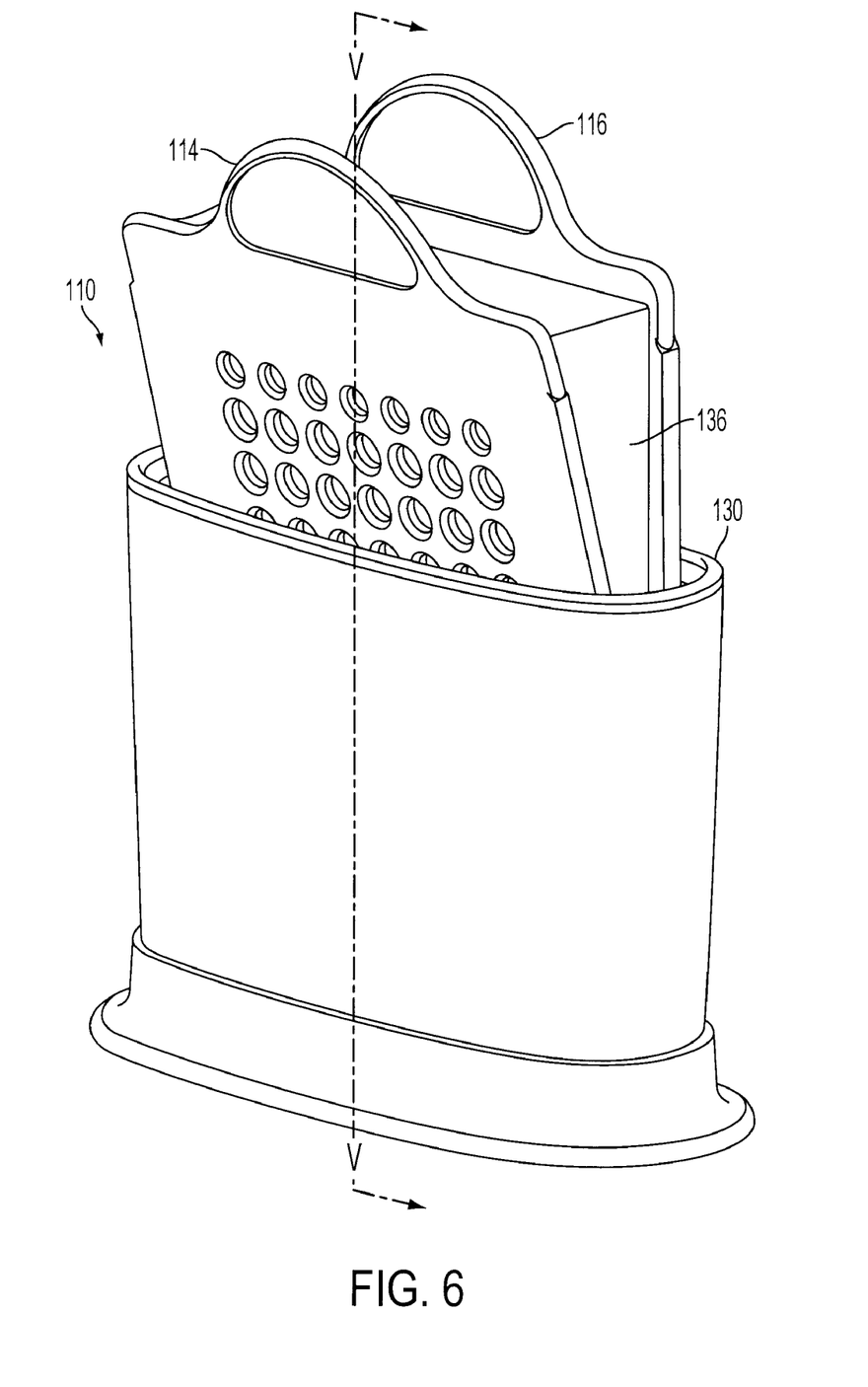
FIG. 6 is a front perspective view of the first embodiment of the sponge cleaning device showing the carrier assembly locked in a position near the apex of its vertical path containing a sponge ready for compression and submersion into the bath.

FIG. 5 is a cross-sectional view of the first embodiment of the cleaning device 110, taken along line V-V of FIG. 6. FIG. 5 shows the carrier assembly 113 locked in a position by a detent 132. Carrier assembly 113 travels in a vertical path into and out of base unit 112. While the carrier assembly 113 is lifted vertically out of base unit 112, a detent 132 presses against the adjacent surface of carrier element 116 and eventually locks into a notch 134. Once detent 132 is locked into notch 134, carrier assembly 113 will remain in position allowing carrier element 114 to open. This position is preferably at a height above the cleaning solution in base unit 112 to allow the carrier assembly 113 and sponge to dry. In order to immerse the carrier assembly 113 and sponge into base unit 112, a user must simply apply a sufficient downward force to the top of carrier assembly 113 to overcome the force applied by detent 132 against notch 134.

FIG. 6 is a front perspective view of the first embodiment of cleaning device 110 showing carrier elements 114 and 116 set in a position and open with a sponge 136 disposed thereon. Carrier elements 114 and 116 remain locked and open in a position near the apex of their vertical path, thus eliminating the need to lift carrier elements 114 and 116 out of the solution in order to insert a sponge.

Figure 7:
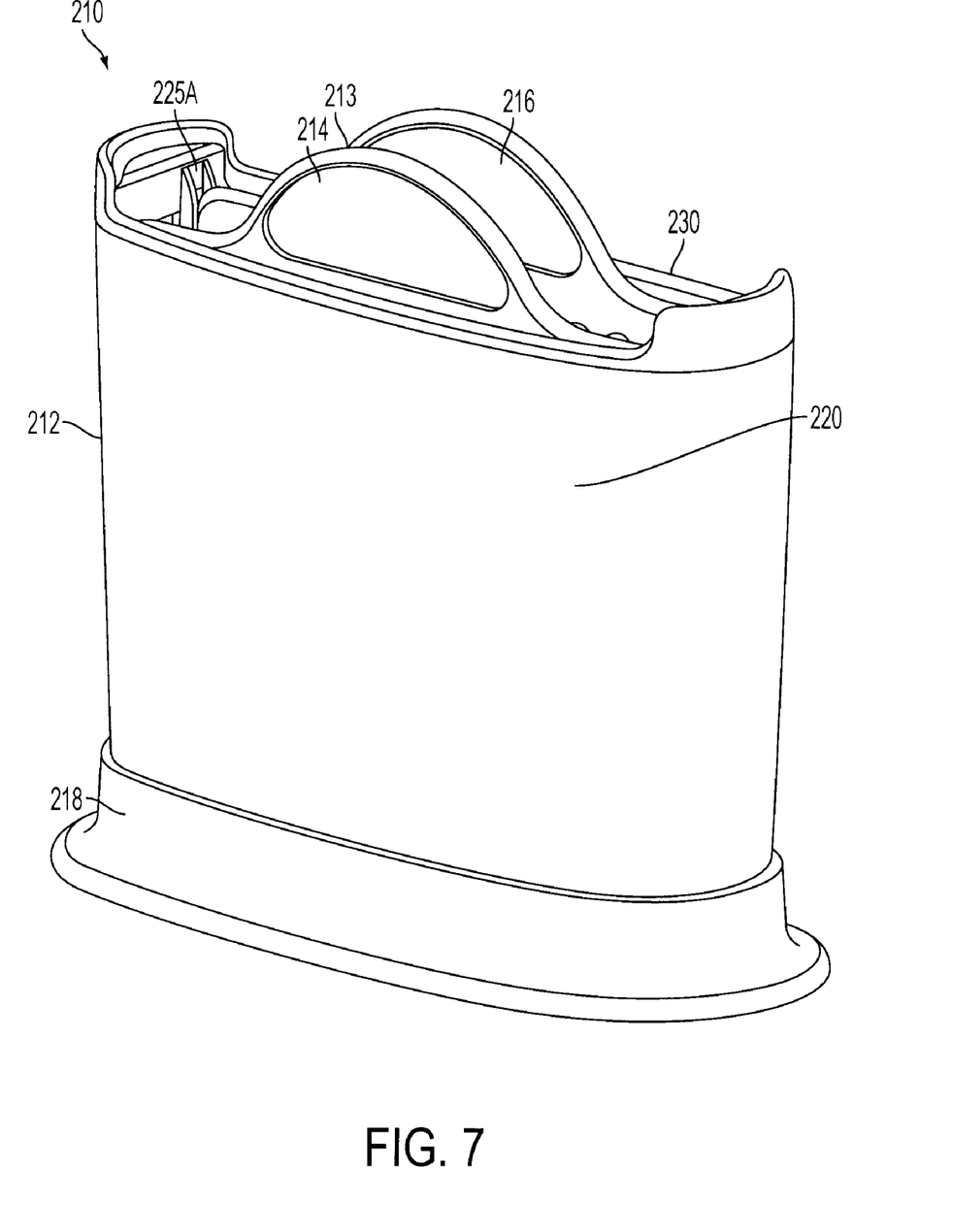
FIG. 7 is a front perspective view of a second embodiment of a sponge cleaning device of the present invention in its closed, immersed state.
Figure 8:
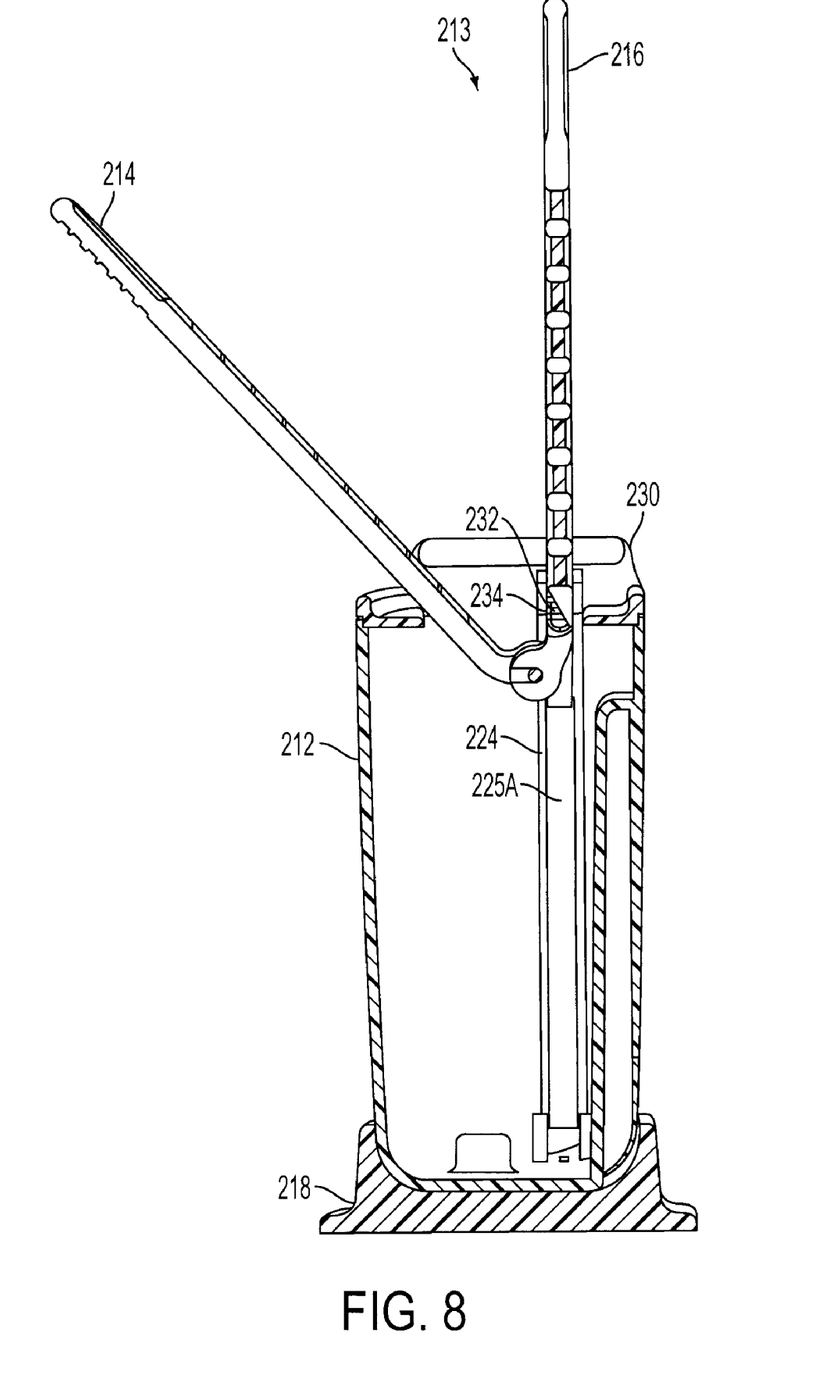
FIG. 8 is a cross-sectional view of the sponge cleaning device of FIG. 9, taken along line VIII-VIII, showing the carrier assembly locked in a position near the apex of its vertical path by a detent. The sponge has been removed for clarity.
Figure 9:
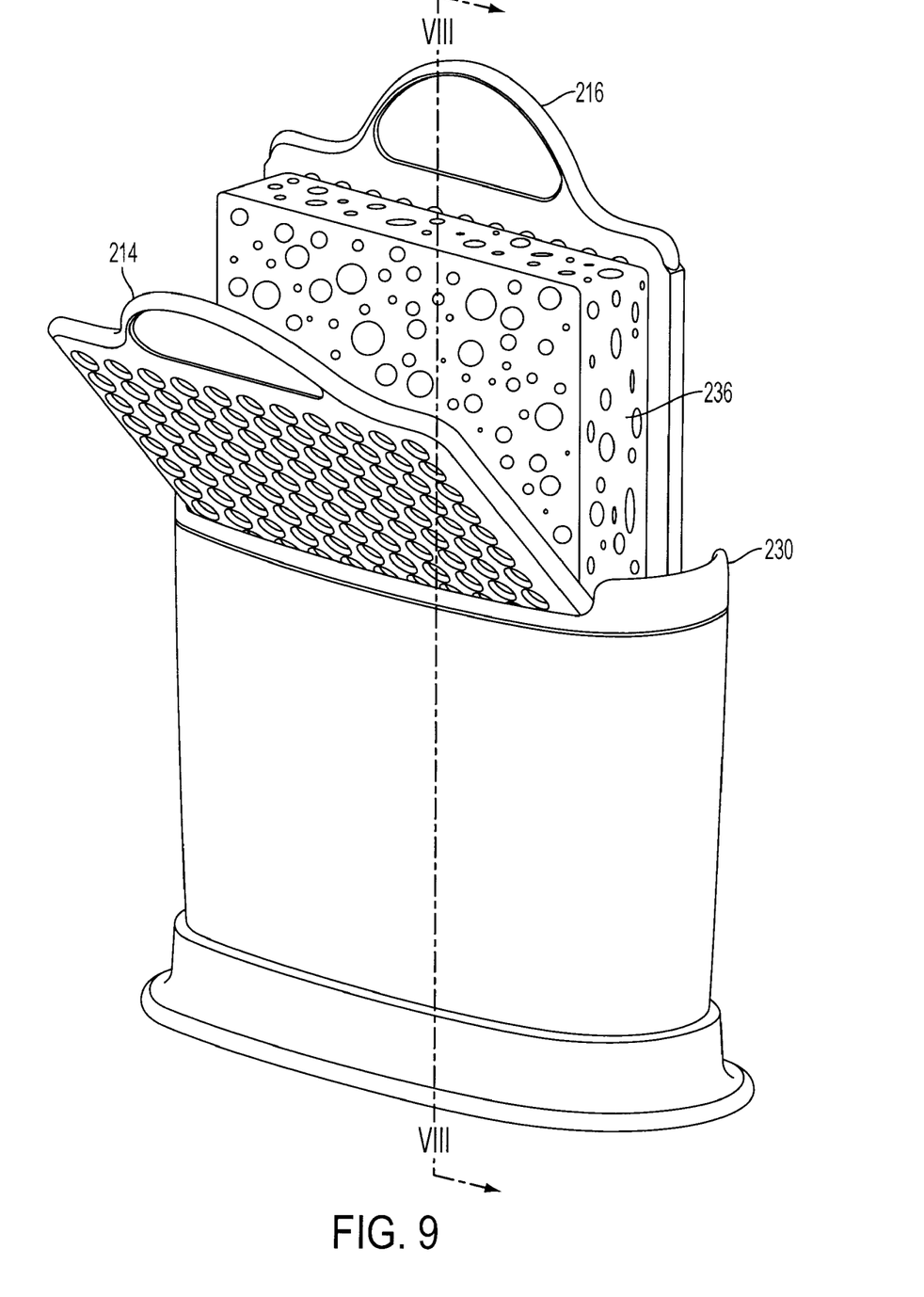
FIG. 9 is a front perspective view of the second embodiment of the sponge cleaning device showing the carrier assembly locked in a position near the apex of its vertical path containing a sponge ready for compression and submersion into the bath.

FIGS. 7-9 depict a second embodiment of the sponge cleaning device of the present invention. The detailed descriptions below discuss the elements of the second embodiment that differ from the first embodiment.

FIG. 7 shows a second embodiment of the sponge cleaning device 210, wherein the cap 230 extends upwards on the sides. This allows guide-tracks for the carrier assembly 213 to extend above the base unit 212. The left guide-track 225A is visible in this figure.

FIG. 8 is a cross-sectional view of the second embodiment of the cleaning device 210, taken along line VIII-VIII of FIG. 9. In this figure, the detent 232 is integrated in the left guide-track 225A of the guide-track system 224. A notch 234 located on the left side of carrier element 216 receives said detent 232. Though not visible from this view, it is to be understood that a corresponding detent in the right guide-track interfaces with a notch the right side of carrier element 216.

FIG. 9 is a front perspective view of the second embodiment of cleaning device 210 showing carrier elements 214 and 216 locked in a position and open with a sponge 236 disposed thereon. The cap 230 extends upwards on both sides allowing the carrier elements 214 and 216 to slide higher out of the base and open wider than cap 130 of the first embodiment would allow. The advantage of this configuration is that sponge 236 can be seated deeper into the jaw-like arrangement of carrier elements 214 and 216, which are hingedly attached at the bottom. When the carrier elements 214 and 216 are squeezed together, the sponge 236 is subjected to more compression than in the first embodiment of the device 210 because the sponge is positioned closer to the hinge that connects carrier elements 214 and 216.

The device may optionally include a spring in the base unit, 112 or 212, to assist with lifting the carrier assembly, 113 or 213, out of the solution and a detent to lock the carrier assembly at a point near the bottom of its vertical path against the spring. The spring may be in the form of, but not limited to, a thin curved piece of plastic with elastic properties. When inserted into the floor of the base unit, 112 or 212, the length of plastic resembles an upside down U. When a downward force is applied by the bottom of the carrier assembly, 113 or 213, the spring would be forced to spread open. The device may also optionally include a detent to resist the upward forces of the spring and keep the carrier assembly, 113 or 213, and sponge, 136 or 236, immersed in solution. The detent would engage at a point near the bottom of the vertical path of the carrier assembly, 113 or 213.

The cleaning device, 110 or 210, can be made of any material that can be easily cleaned by hand or machine, preferably plastic. The dimensions of the device, 110 or 210, can also be increased in order to fabricate a device that can accommodate larger sponges. By using plastic as the material of construction the parts of the cleaning device, 110 or 210, can be easily and inexpensively fabricated through molding. Plastic is also light-weight; therefore, it is advantageous in the fabrication of a cleaning device of large dimensions that is made to accommodate larger sponges. It is also critical that the material of construction for the cleaning device, 110 or 210, is compatible with the type of cleaning solution with which it is filled.

The cleaning solution can be any of various effective cleaning solutions including, but not limited to, a disinfectant or sanitizer. This solution could be of an environmentally friendly nature. The solution should also be non-caustic and non-irritant due to the risk of exposure to skin when using a sponge that is cleaned by the device or when filling the device, 110 or 210, with the cleaning solution. As used herein, "disinfectant" means a solution applied to surfaces and objects to destroy or irreversibly inactivate infectious fungi and bacteria, but not necessarily their spores. As used herein, "sanitizer" means a solution applied to surfaces and objects to reduce, but not necessarily eliminate, microorganisms to levels considered safe as determined by public health codes or regulations.

Because disinfectants are capable of completely destroying specific microorganisms, it is preferred that the cleaning solution is a disinfectant that destroys the bacteria that are commonly in contact with the sponge 136 or 236, thereby ensuring optimal decontamination.

The above-described embodiments are intended to illustrate the principles of the invention, but not to limit its scope. Other embodiments and variations will be apparent to those skilled in the art and may be made without departing from the spirit and scope of the invention.

We claim:

1. A method for sanitizing a sponge used for cleaning, comprising the steps of:
   a. inserting a sponge to be sanitized into a device comprising:
      a base unit, comprising a top opening, an interior floor, and walls of sufficient dimensions to contain a bath of enough cleaning solution to fully engulf a sponge;
      a carrier assembly comprising a pair of generally planar carrier elements for supporting a sponge in vertical orientation for insertion and withdrawal from the base unit, each carrier element having a multiplicity of channels to facilitate movement of liquid into and out of the sponge; and
      a guide-track system in the base unit to stabilize the carrier assembly along a vertical path during insertion and withdrawal from the base unit,
   b. compressing the sponge in the carrier assembly;
   c. lowering the compressed carrier assembly and sponge into the base unit to immerse the sponge in a cleaning solution;
   d. releasing compression to allow the sponge to absorb the cleaning solution;
   e. compressing the sponge again to expel absorbed liquid or foreign matter;
   f. raising the compressed carrier assembly and sponge from the cleaning solution; and
   g. removing the sponge from the device.

2. A method for using, a device for sanitizing a sponge used for cleaning, the device comprising:
   a base unit, comprising a top opening, an interior floor, and walls of sufficient dimensions to contain a bath of enough cleaning solution to fully engulf a sponge;
   a carrier assembly comprising a pair of generally planar carrier elements for supporting a sponge in vertical orientation for insertion and withdrawal from the base unit; and
   a guide-track system in the base unit to stabilize the carrier assembly along a vertical path during insertion and withdrawal from the base unit, the guide-track system containing a detent at the top of the carrier assembly's vertical path,
   wherein each carrier element has a multiplicity of channels to facilitate movement of liquid into and out of the sponge, the method comprising the steps of:
   a. compressing a sponge in the carrier assembly;
   b. lowering the compressed carrier assembly and sponge into the base unit to immerse the sponge in a cleaning solution;
   c. releasing compression to allow the sponge to absorb the cleaning solution;
   d. compressing the sponge again to expel absorbed liquid or foreign matter;
   e. raising the compressed carrier assembly and sponge from the cleaning solution until the carrier assembly locks into position at the top of its vertical path;
   f. allowing the sponge to dry; and
   g. removing the sponge from the device.

* * * * *